(12) United States Patent
Toraya et al.

(10) Patent No.: US 9,146,203 B2
(45) Date of Patent: Sep. 29, 2015

(54) X-RAY STRESS MEASURING APPARATUS

(75) Inventors: Hideo Toraya, Tachikawa (JP); Shigeru Munekawa, Tokyo (JP)

(73) Assignee: RIGAKU CORPORATION, Tokyo (JP)

(*) Notice: Subject to any disclaimer, the term of this patent is extended or adjusted under 35 U.S.C. 154(b) by 189 days.

(21) Appl. No.: 13/812,575

(22) PCT Filed: Jul. 29, 2011

(86) PCT No.: PCT/JP2011/067517
§ 371 (c)(1),
(2), (4) Date: Jan. 28, 2013

(87) PCT Pub. No.: WO2012/015046
PCT Pub. Date: Feb. 2, 2012

(65) Prior Publication Data
US 2013/0121470 A1    May 16, 2013

(30) Foreign Application Priority Data

Jul. 30, 2010    (JP) ................................. 2010-172594

(51) Int. Cl.
| | |
|---|---|
| G01N 23/20 | (2006.01) |
| G01N 23/207 | (2006.01) |
| G01L 1/25 | (2006.01) |
| G01L 1/00 | (2006.01) |
| G01B 15/00 | (2006.01) |

(52) U.S. Cl.
CPC ............... *G01N 23/207* (2013.01); *G01L 1/25* (2013.01); *G01L 1/255* (2013.01); *G01N 23/20075* (2013.01); *G01B 15/00* (2013.01); *G01L 1/00* (2013.01); *G01N 23/20* (2013.01)

(58) Field of Classification Search
CPC . G01N 23/20; G01N 23/20075; G01B 15/00; G01L 1/00; G01L 1/25; G01L 1/255
USPC ................................................ 378/70–72, 210
See application file for complete search history.

(56) References Cited

U.S. PATENT DOCUMENTS 4,489,425 A * 12/1984 Borgonovi ...................... 378/72
7,646,847 B2    1/2010 He et al.
(Continued)

FOREIGN PATENT DOCUMENTS

| JP | 49-119686 | 11/1974 |
|---|---|---|
| JP | 51-31255 | 3/1976 |

(Continued)

*Primary Examiner* — Anastasia Midkiff
(74) *Attorney, Agent, or Firm* — Mattingly & Malur, PC (57) ABSTRACT

An X-ray stress measuring apparatus, for measuring stress on a sample, comprises: a pair of X-ray generating means (10, 11, 10', 11') for irradiating X-ray beams, determining an angle defined between the X-ray beams, mutually, at an arbitrary fixed angle, on a plane inclining by an angle desired with respect to a surface of the sample to be measured stress thereon; an X-ray sensor portion (29) for detecting plural numbers of Debye rings (C, C'), which are generated by incident X-ray beams from said pair of X-ray generating means; and a battery (410) for supplying necessary electricity to each of parts of the apparatus, wherein said X-ray sensor portion is made up with only one (1) piece of a 2-dimensional X-ray detector (20) or a 1-dimensional X-ray detector (20'), and is disposed in a position where the plural numbers of Debye rings generated by the incident X-ray beams from the at least one pair of X-ray generating means are adjacent to each other, or intersect with each other, thereby detecting the plural numbers of the Debye rings caused due to the X-ray and the X'-ray in common with.

12 Claims, 7 Drawing Sheets

(56) References Cited

U.S. PATENT DOCUMENTS

| | | |
|---|---|---|
| 2006/0098779 A1 | 5/2006 | Turner |
| 2009/0225944 A1* | 9/2009 | Lee et al. ................. 378/71 |

FOREIGN PATENT DOCUMENTS

| | | |
|---|---|---|
| JP | 63-134942 | 6/1988 |
| JP | 2-266249 | 10/1990 |
| JP | 4-189451 | 7/1992 |
| JP | 8-102890 | 4/1996 |
| JP | 10-185842 | 7/1998 |
| JP | 2002-39970 | 2/2002 |
| JP | 2003-66151 | 3/2003 |
| JP | 2007-524234 | 8/2007 |
| JP | 2007-529004 | 10/2007 |
| JP | 2007-530979 | 11/2007 |
| WO | WO 2005/065333 A2 | 7/2005 |
| WO | WO 2005/078477 A1 | 8/2005 |

* cited by examiner

X-RAY STRESS MEASURING APPARATUS

TECHNICAL FIELD OF THE INVENTION

The present invention relates to an X-ray stress measuring apparatus for measuring stress in a sample with applying X-ray, and in particular, it relates to an X-ray stress measuring apparatus, which can be achieved as a portable apparatus, because it can be constructed to be relatively small in sizes and light in the weight thereof.

BACKGROUND OF THE INVENTION

Analyses of various kinds of samples with using the X-ray (s) are adopted widely, in particular, in a field of so-called a non-destructive analysis, for example, because of not accompanying disassembly of the sample. Conventionally, for example, in the following Patent Document 1 is already known a hand-held type X-ray diffractometer, mounting an X-ray generating apparatus and a 2-dimentional (or, area) X-ray detector and being portable.

On the other hand, for the purpose of detecting intensity of the X-ray diffraction or the like, although an imaging plate (IP), such as, a photo-sensitive film, etc., has been used, in general; however, accompanying with a remarkable development of a semiconductor manufacturing technology in recent years, various kinds of X-ray detectors are developed. For example, in the following Patent Document 2 is already disclosed a photon counting mode (PCM) detector equipped with plural numbers of pixels, in which a cadmium zinc telluride (CZT) detector and an ASIC chip mounting one (1) or more number(s) of read-out circuit(s) thereon are combined with. Also, in the following Patent Document 3 is already known a method for monitoring a dose of radioactivity corrected on the pixel and an X-ray detector for the same, in particular, in an apparatus equipped with plural numbers of such pixels. And, in the following Patent Document 4 is also already known an X-ray imaging device applying a semiconductor X-ray array detector therein.

Furthermore, in the following Patent Document 4 is also already known the structure for achieving a compactification of detector (i.e., a compact detector), and also for eliminating a dead space, which is generated when aligning the plural numbers the detectors each having a unit of pixels.

PRIOR ART DOCUMENTS

Patent Documents

[Patent Document 1] U.S. Pat. No. 7,646,847;
[Patent Document 2] Japanese Patent Laying-Open for PCT No. 2007-524234 (2007);
[Patent Document 3] Japanese Patent Laying-Open for PCT No. 2007-529004 (2007);
[Patent Document 4] Japanese Patent Laying-Open No. Hei 8-102890 (1996); and
[Patent Document 5] Japanese Patent Laying-Open No. 2003-66151 (2003).

With such conventional technologies as mentioned above, in particular, the portable X-ray diffractometer of hand-held type disclosed in the above Patent Document 1 needs plural numbers of 2-dimennsional (i.e., area) X-ray detectors or 1-dimensional (e.g., line) X-ray detectors, being made from semiconductor, for detecting a pattern of the X-ray (in particular, the Debye ring) diffracted by a sample. However, under the present situation, such semiconductor X-ray detectors are expensive, and they come to be relatively large in the sizes thereof, if combining related parts with; i.e., not having such the structures suitable for building up the portable apparatus of hand-held type, necessarily.

Then, according to the present invention, being accomplished by taking the drawbacks of the conventional technologies mentioned above into the consideration thereof, an object thereof is to provide an X-ray stress measuring apparatus for measuring stress on a sample with applying the X-ray, and in particular, the hand-held type X-ray stress measuring apparatus, being actually portable, having structures suitable for small-sizing and light-weight of the apparatus.

BRIEF SUMMARY OF THE INVENTION

According to the present invention, for accomplishing the object mentioned above, first of all, there is provided an X-ray stress measuring apparatus, for measuring stress on a sample, comprising, at least: a pair of X-ray generating means for irradiating X-ray beams, determining an angle defined between the X-ray beams, mutually, at an arbitrary fixed angle, on a plane inclining by an angle desired with respect to a surface of the sample to be measured stress thereon; an X-ray sensor portion for detecting plural numbers of Debye rings, which are generated by incident X-ray beams from said pair of X-ray generating means; and a battery means for supplying electricity to said pair of X-ray generating means and said X-ray sensor portion, wherein said X-ray sensor portion is made up with one (1) piece of a 2-dimensional X-ray detector or a 1-dimensional X-ray detector, and is disposed in a position where the plural numbers of Debye rings generated by the incident X-ray beams from said at least one pair of X-ray generating means are adjacent to each other, or intersect with each other.

Also, according to the present invention, within the X-ray stress measuring apparatus, as described in the above, it is preferable that the angle mutually defined between the X-ray beams of said pair of X-ray generating means is within a range from 20 degrees to 170 degrees, and further that the angle mutually defined between the X-ray beams of said pair of X-ray generating means is at 90 degrees. And, it is preferable that said X-ray sensor portion is made up with the 2-dimensional X-ray detector, further comprising means for determining due to which one of the X-ray beams incident upon said sample from said pair of X-ray generating means said ring is caused, upon basis of the Debye rings detected by said 2-dimensional X-ray detector, and further that said 2-dimensional X-ray detector is fixed at a position and an angle, which are predetermined with respect to said pair of X-ray generating means, within a space defined between said pair of X-ray generating means.

Also, according to the present invention, in the X-ray stress measuring apparatus, as described in the above, it is preferable that said X-ray sensor portion is made up with the 1-dimensional X-ray detector, further comprising means for driving said pair of X-ray generating means, selectively, on a time sequence, and further that said 1-dimensional X-ray detector is fixed at a position and an angle, which are predetermined with respect to said pair of X-ray generating means, within a space defined between said pair of X-ray generating means.

In addition to the above, according to the present invention, the X-ray stress measuring apparatus as described in the above, preferably, further comprises a radiation shielding member for storing said X-ray sensor portion, together with said pair of X-ray generating means therein, in such case, preferably further comprises a grip portion attached on said radiation shielding member in one body. Further, the X-ray stress measuring apparatus, as described in the above, preferably, further comprises a trigger disposed in a position adjacent to said grip portion, for instructing an X-ray stress measuring operation of said X-ray stress measuring apparatus, and further it is preferable that said battery means is stored within said grip portion, and further, said battery means is a rechargeable battery. And, it is preferable to further comprises a display position for display a result of X-ray stress measurement by said X-ray stress measuring apparatus, on an outside of said radiation shielding member.

Effect(s) of the Invention

According to the present invention mentioned above, the following very superior effect can be achieved; i.e., it is possible to provide the hand-held type X-ray stress measuring apparatus having structures suitable for small-sizing and light-weight of the apparatus, and therefore being actually portable.

DETAILED DESCRIPTION OF THE PREFERRED EMBODIMENTS

Hereinafter, explanation will be given, fully in details thereof, on an X-ray stress measuring apparatus, according to the embodiments of the present embodiment, by referring to the drawings attached herewith.

Figure 1:
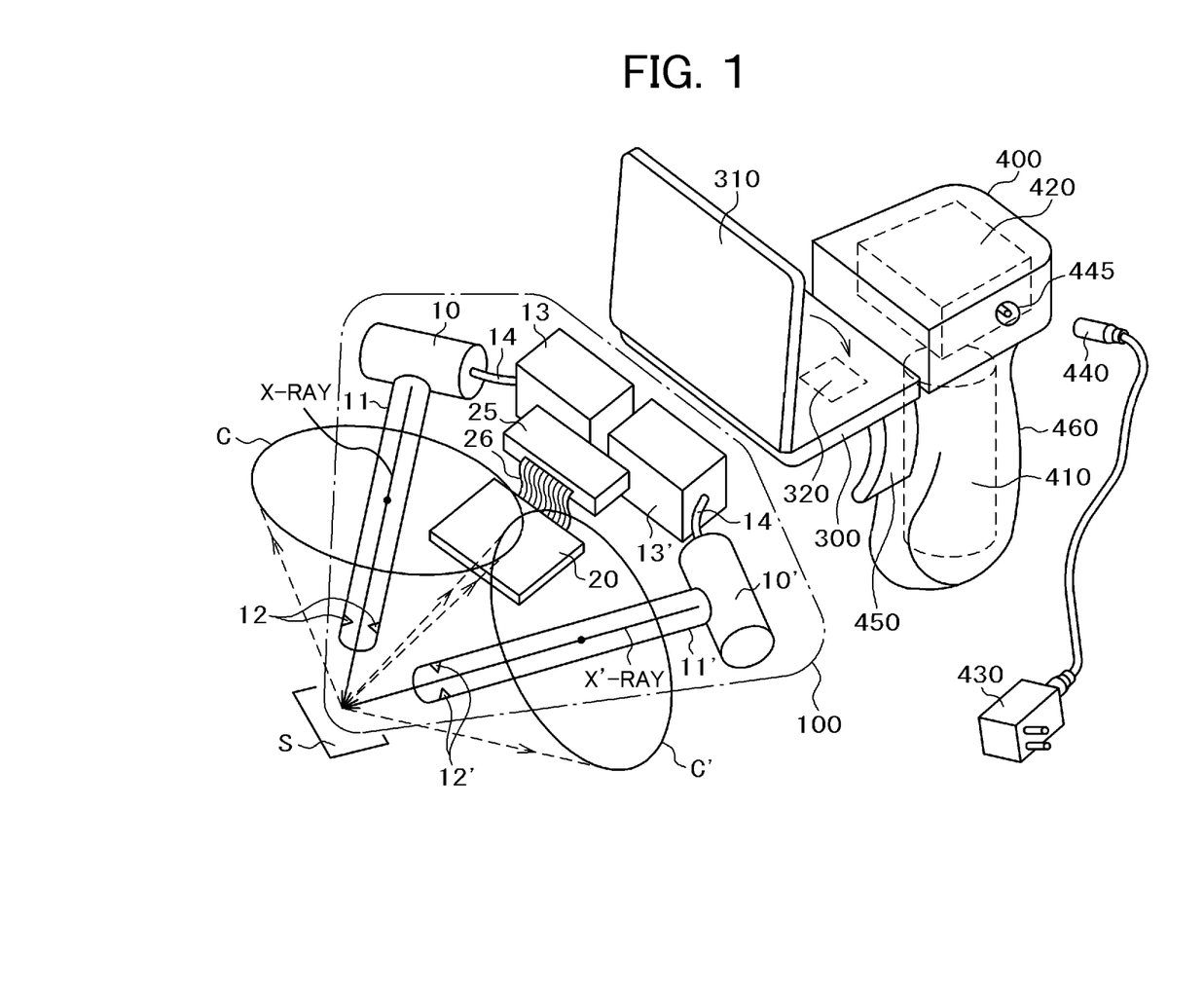
FIG. 1 is an entire perspective view for showing the entire structure of an X-ray stress measuring apparatus, according to an embodiment of the present invention, displaying a part thereof transparently.

First of all, FIG. 1 shows the entire structures of an X-ray stress measuring apparatus, according to the present invention. In this figure, reference numerals 10 and 10' depict a pair of X-ray tubes, i.e., small-size X-ray sources, which are provided within that apparatus, wherein each comprises a collimator 11 or 11' extending from a window, i.e., forming an optical path for taking out an X-ray therefrom. However, as a target material composing the X-ray tube 10 or 10', chromium, cobalt, iron, copper, molybdenum or other metal material(s), for example, are suitable. Also, at a tip portion of the collimator 11 or 11' is attached a slit 12 or 12' for defining the X-rays from the X ray source into a beam having a desired diameter. However, although not illustrated herein, a filter member or a monochromator, etc., may be disposed in an inside of the collimator 11 or 11', for example, and therefore, a monochromatic X-ray beam can be obtained from the X-ray source mentioned above.

The X-ray beams (X-ray, X'-ray, respectively) from that pair of X-ray tubes, i.e., a first X-ray tube 10 and a second X-ray tube 10' are, as apparent from the figure, incident upon a surface of a sample S while keeping an angle defined between the X-ray beams, mutually, at an arbitrary fixed angle, within a surface inclining by an arbitrary angle with respect to the surface of the sample S. The arbitrary fixed angle defined between the pair of X-ray beams is determined within a range from 20 degrees to 170 degrees, and in particular, it is preferable to determine this angle within a range from 70 degrees to 110 degrees. For example, they are incident upon the surface of that sample S while being directed into such directions as to define 90 degrees therebetween. And, with doing this, as shown in the figure, due to incidence of the pair of X-ray beams mentioned above upon the sample S, the diffracted X-rays, i.e., Debye rings C and C' (e.g., a diffraction cone) are generated. And, at the position where the pair of Debye rings intersect with each other, between the pair of the X-ray tubes 10 and 10', or in a space defined between the collimators 11 and 11', there are disposed a 2-dimensional (i.e., the area) sensor 20 made from semiconductor, the details of which will be mentioned hereinafter. Thus, this 2-dimensional (i.e., the area) sensor 20 is used, in common, i.e., for detecting parts of the Debye rings, respectively, which are generated due to the X-ray beams (e.g., the X-ray and X'-ray) from the first X-ray tube 10 and the second X-ray tube 10'.

Also, in this FIG. 1, reference numerals 13 and 13' depict high-voltage generating portions, for supplying high-voltages to the first X-ray tube 10 and the second X-ray tube 10', respectively. Each of them, though not shown in the figure, is made up with a circuit (for example, a Cockcroft-Walton high-voltage booster rectifying circuit) connecting a large number of chip capacitors and/or chip diodes alternately on a ceramic substrate, and it supplies high-voltage through a high-voltage cable 14 or 14', so as to generate the X-ray beam. Also, a reference numeral 25 in the figure, although the details thereof will be mentioned later, depicts a signal processing portion, for receiving parts of the diffracted X-rays, e.g., the Debye rings C and C', which are detected by the 2-dimensional (i.e., the area) sensor 20 mentioned above, in the form of electric signals, and thereby processing a predetermined process(es) thereupon and outputting them, and this may be constructed with a CPU (Central Processing Unit) and/or various kinds of memories, etc., included therein. Further, a reference numeral 26 depicts a signal cable for transmitting the electric signals from the X-ray sensor 20. Further, the parts mentioned in the above are covered with a resin molding mixing a heavy metals therein, such as, tungsten (W), tantalum (Ta) or lead (Pb), etc; thereby building up a radiation shield 100. Also, but not illustrated herein, within the radiation shield 100 may be disposed a small-size gas adhesion pump or vacuum pump, and thereby to keep an optical paths for the X-ray beams (i.e., the X-ray and X'-ray) in the vacuum condition.

Furthermore, in FIG. 1, behind the radiation shield (or a cover) 100 mentioned above is attached a controller portion 300, in one body, having a foldable display portion (for example, a liquid crystal display device) 310. Further, this controller portion 300 comprises a controlling portion 320 (for example, including a CPU (Central Processing Unit) and/or various kinds of memories, etc.) for controlling that X-ray stress measuring apparatus as a whole, and also, though not shown in the figure herein, an input portion (e.g., various kinds of input buttons, etc.), which is necessary for operations of that apparatus, and there by building up the input portion. Also, on the display portion 310 can be display an image of the Debye rings C and C' (e.g., the diffraction cone) obtained by the 2-dimensional (i.e., the area) X-ray sensor 20 mentioned above, and/or a result of measurement/analysis obtained from the signal processing portion 25 mentioned above.

And, behind the controller portion 300 mentioned above, as well as, a power source portion 400 for supplying necessary electric power to each portion of the apparatus mentioned above, there is further attached a trigger (e.g., a switch) 450, for instructing an operation for measuring stress with using the X-ray to the apparatus under the condition that a user holds that apparatus, in a grip portion 460, in one body. Further, a reference numeral 410 in the figure depicts a battery (for example, a rechargeable battery) composing the power source portion 400, and a reference numeral 420 depicts an electric power converter portion, for converting electric power of battery 410 to a predetermined voltage, to be supplied to each portion, and also for inputting an AC power from a plug 430, which is connectable with a commercial power source (via adapters shown by reference numerals 440 and 445, in the figure) so as to convert it into DC power, thereby storing electricity into the battery 410.

Figure 2:
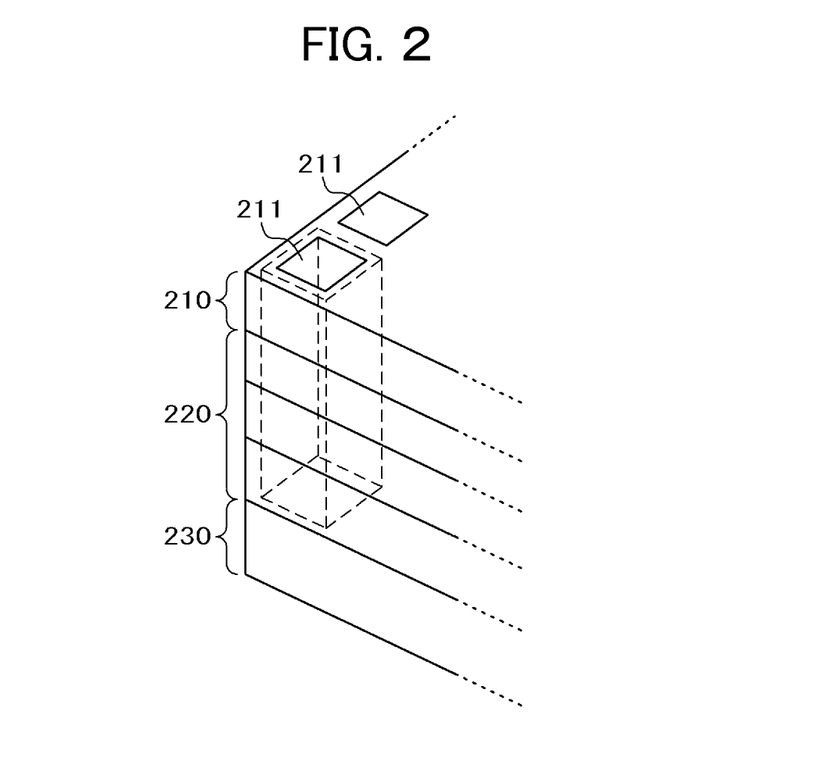
FIG. 2 is a partially enlarged perspective view for showing the detailed structures of an X-ray sensor portion for building up the X-ray stress measuring apparatus mentioned above.

Next, in FIG. 2 attached herewith is shown an example of the detailed structures of the X-ray sensor portion 20 mentioned above. In this figure, a reference numeral 210 depicts so-called a semiconductor X-ray sensor portion, being made of CdTe, CdZnTe, etc., for example, and as apparent from the figure, on which a large number of pixels (487×487 pieces) 211 are formed, each having an outer shape being nearly square, for example, 172 μm×172 μm. However, although not shown in the figure herein, at a central part of each pixel is formed an X-ray detecting portion, and on one surface thereof (an upper surface side in the figure) is formed a bias electrode for applying negative voltage, with using a transparent material (see a reference numeral 214 in FIG. 3), such as, ITO (Indium Tin Oxide), etc., while on the other surface thereof (a lower surface side in the figure) is formed so-called a detecting electrode (see a reference numeral 213 in FIG. 3), for detecting an electron(s) generated by an energy of the X-ray.

Further, on the lower surface of the semiconductor X-ray sensor portion 210 is provided a read-out portion 220, having the similar configuration thereto, which is built up with so-called an ASIC (Application Specific Integrated Circuit). This read-out portion 220 is built up with plural numbers of layers (in the present example, three (3) layers), being piled up, wherein various circuits are constructed in 3-dimensional manner, by establishing electrical connection between the layers, respectively, through a through Si via (i.e., an electrode, perpendicularly penetrating through an inside of the semiconductor chip made of silicon). Below this read-out portion 220, there are further provided a large number of pads, corresponding to each pixel, and further, they are led to a wiring portion 230, which is made of wire bonding pats. Not shown in the figure herein, by means of a parallel/serial converter or a channel switch or a multiplexer, etc., which is provided in an inside thereof, a number of outputs thereof is reduced down, and is outputted through terminals (or cables), which are provided in a side wall portion thereof.

Figure 3:
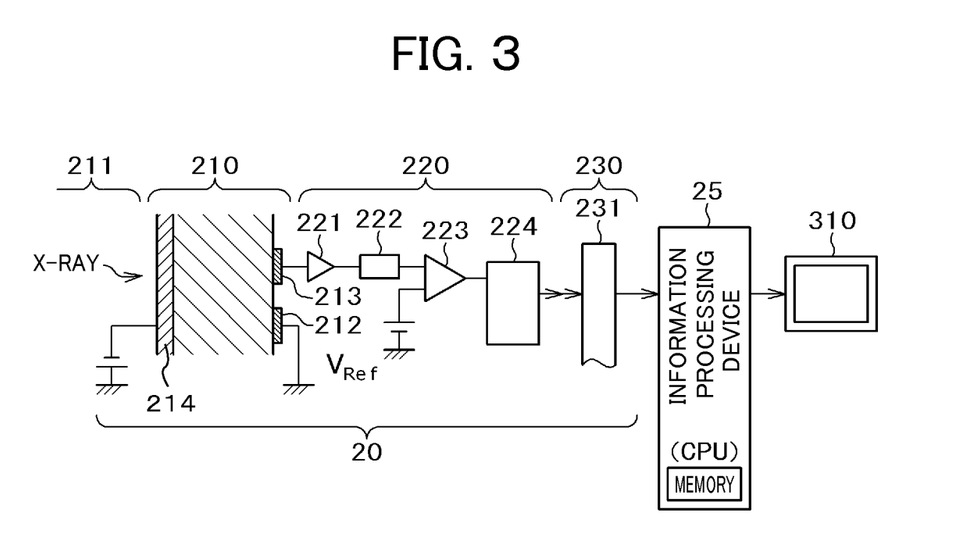
FIG. 3 is a block diagram for showing the circuitry structure of the X-ray stress measuring apparatus, including the X-ray sensor portion for building up the X-ray stress measuring apparatus mentioned above.

Following to the above, FIG. 3 attached herewith shows the circuit structures of the X-ray stress measuring apparatus as a whole thereof, including the X-ray sensor 20, having the semiconductor X-ray sensor portion 210, the read-out portion 220 and further the wiring portion 230 mentioned above, and furthermore, including the signal processing portion 25 mentioned above therein. Thus, the reference numeral 214 depicts the bias electrode mentioned above, made of the transparent ITO, 212 a ground electrode, and 213 the detecting electrode, respectively. Also, a reference numeral 221 in the figure depicts an amplifier for amplifying the detected signal to have a desired amplitude thereof, 222 a wave shaping circuit for shaping the waveform of the signal amplified, 223 a comparator for comparing an output from the waveform shaping circuit mentioned above to a comparison reference voltage $V_{Ref}$, and 224 a counter circuit for counting up the outputs from the comparator circuit mentioned above, respectively. In addition thereto, on the wiring portion 230 are provided the wire bonding pads 231 mentioned above.

Thus, as is apparent from the FIG. 3 mentioned above, the signals detected from the large number of X-ray sensors (i.e., pixels), building up the semiconductor X-ray sensor portion 210 mentioned above, are led to the read-out portion 220, which is disposed on the reverse surface thereof, and after being treated with the predetermined processes) thereon within the processing circuits, which are formed by a large number thereof in an inside thereof with the ASIC, they are inputted into the information processing portion of device 25, being constructed by including the CPU, through the wiring portion 230. The information processing device 25 executes stress measuring/analyzing processes, which will be mentioned hereinafter, upon basis of the information of the diffracted X-rays obtained in this manner, and further, displays a result thereof on the display portion (e.g., the display device) 310. Also, with such X-ray sensor 20 as was mentioned above, it is possible to detect the intensity of the X-ray a each X-ray sensor (or the pixel), and for example, it is possible to display the intensity in the gradation of $2^{19}=524288$.

Figure 4A:
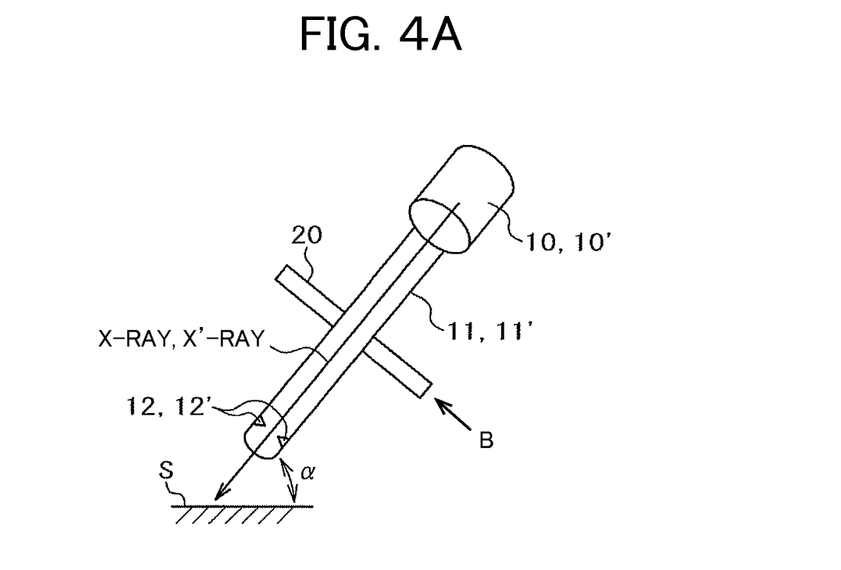
FIGS. 4A and 4B are views for explaining about the details of an arrangement of a semiconductor X-ray sensor portion and a pair of X-ray tubes within the X-ray stress measuring apparatus mentioned above.
Figure 4B:
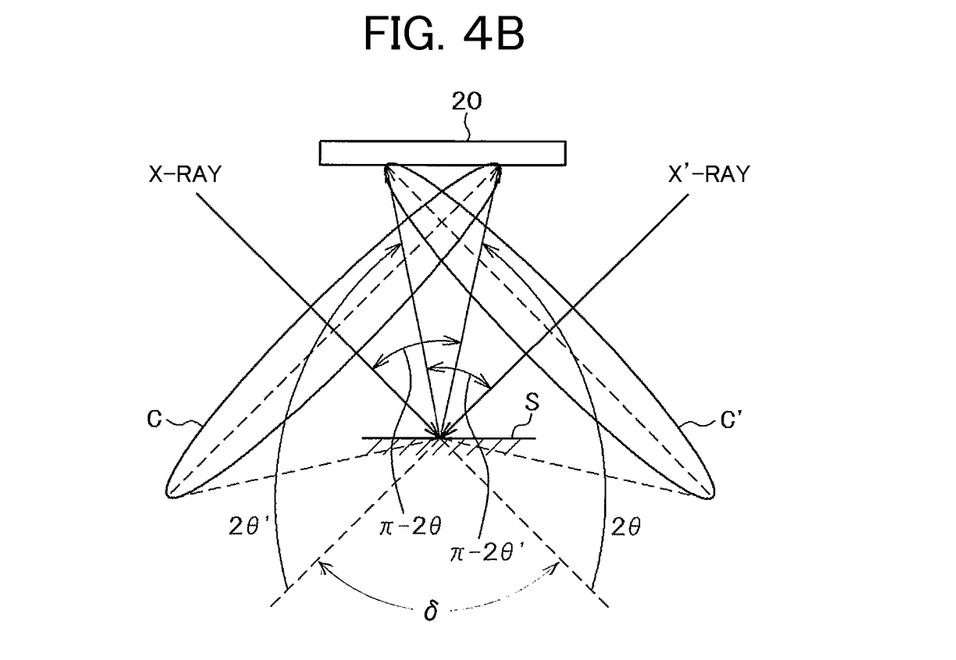

Following to the above, explanation will be given on the arrangement of the semiconductor X-ray sensor portion 20 and the pair of X-ray tubes (e.g., the first X-ray tube 10 and the second X-ray tube 10') mentioned above, by referring to FIGS. 4A and 4B attached herewith. Firstly, FIG. 4A shows the condition of seeing the pair of X-ray tubes 10 and 10' from a side thereof, and in this figure, that pair of X-ray tubes 10 and 10' enter the X-ray bean and the X'-ray beam upon the surface of the sample S, respectively, on a surface inclining by an angle α. FIG. 4B shows the condition of seeing FIG. 4A in the direction of an arrow B shown therein, wherein an angle δ, being defined by the beam entering on the surface of the sample S from the first X-ray tube 10 and the beam entering on the same from the second X-ray tube 10', is determined at an arbitrary fixed angle. The angle δ defined by the pair of X-ray beams is fixed at one (1) angle, within a range from 20 degrees to 170 degrees, but it may be fixed at 90 degrees, for example. In case where they are so determined that they define the right angle (i.e., 90 degree), mutually, then as a result thereof, as is shown in FIG. 4B, the Debye rings C and C' (i.e., the diffraction cone) are generated centering around the respective beams due to the incidences of both the X-ray beams. And, those Debye rings C and C' changes an angle of the cone (π-2θ, π-2θ') depending on presence of the stress, in particular, when the sample is a polycrystalline metal; however, normally, they are formed at positions, being adjacent to each other, or intersecting with each other (2θ, 2θ'=96-162 degrees, approximately). Then, the 2-dimensional (or the area) sensor portion 20 mentioned above is arranged at the position where the pair of Debye rings C and C' are adjacent to each other or intersect with each other. Namely, the pair of X-ray tubes mentioned above (i.e., the first X-ray tube 10 and the second X-ray tube 10') are disposed at the position and the angle, which are determined in advance with respect to the semiconductor X-ray sensor portion 20, and in particular, it may be preferable that those are disposed, symmetrically to each other, with respect to a center of the semiconductor X-ray sensor portion. Even in case where the angle δ defined by the pair of X-ray beams is determined at an angle other than the right angle (90 degree), the angles of the Debye rings C and C' (i.e., the diffraction cone) have the values (π-2θ, π-2θ'), respectively, i.e., being same to the case where the angle δ=90 degrees, therefore the present invention is still effective even when that angle is the arbitrary fixed angle.

Namely, by driving the pair of X-ray tubes (e.g., the first X-ray tube 10 and the second X-ray tube 10') mentioned above, simultaneously (or, entering the X-ray and the X'-ray, simultaneously), it is possible to detect the Debye rings C and C' (i.e., the diffraction cones), which are formed at the positions, being adjacent to each other or intersecting with each other, simultaneously, on the semiconductor X-ray sensor portion 20 mentioned above, and also by comparing radiuses of those Debye rings C and C' or angles (π-2θ, π-2θ') of the cones, it is possible to detect presence of the stress upon the sample S mentioned above, as well as, a direction thereof. Or alternatively, by comparing those with the radius or the angle (π-2θ), which is measured in advance, under the condition where no stress is applied thereupon, it is also possible to measure a magnitude thereof.

Figure 5A:
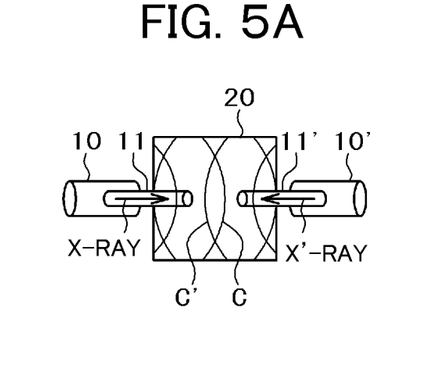
FIGS. 5A and 5B are views for explaining a relationship of dispositions between the semiconductor X-ray sensor portion and the pair of X-ray tubes mentioned above.
Figure 5B:
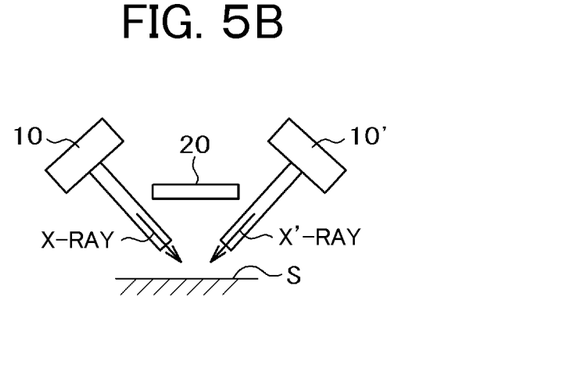
Figure 6A:
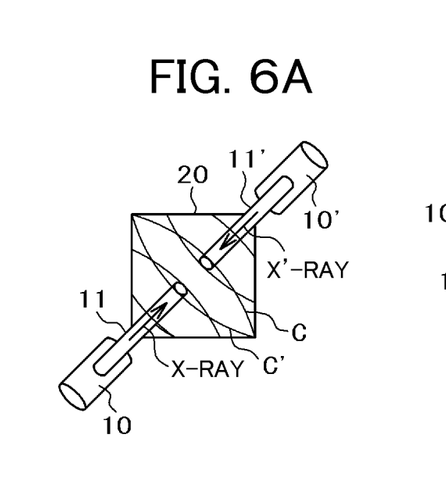
FIGS. 6A and 6B are views for explaining other relationship of dispositions between the semiconductor X-ray sensor portion and the pair of X-ray tubes mentioned above.
Figure 6B:
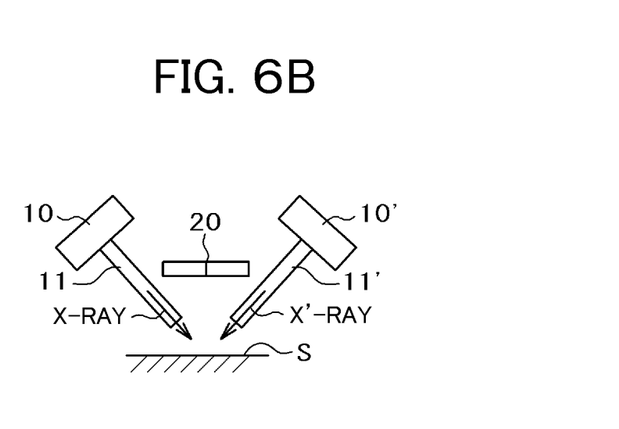
Figure 7A:
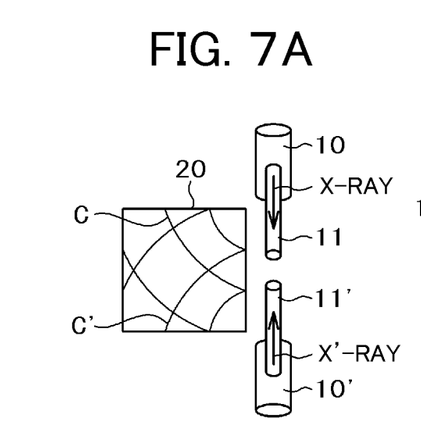
FIGS. 7A and 7B are views for explaining further other relationship of dispositions between the semiconductor X-ray sensor portion and the pair of X-ray tubes mentioned above.
Figure 7B:
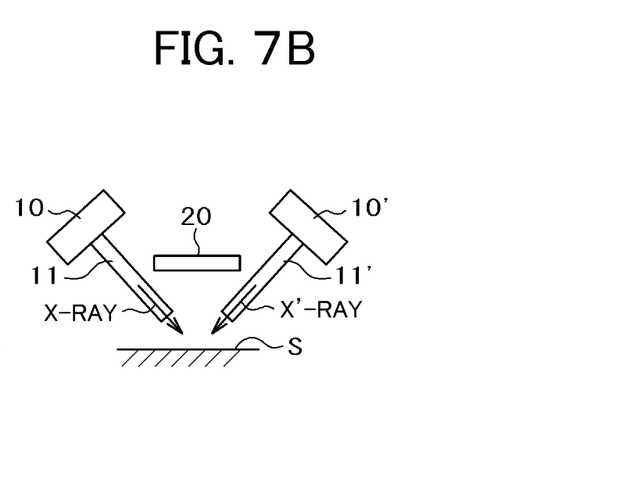

Next, FIGS. 5A and 5B, FIGS. 6A and 6B, and FIGS. 7A and 7B show various configurations of arrangement of the semiconductor X-ray sensor portion 20 and the pair of X-ray tubes (e.g., the first X-ray tube 10 and the second X-ray tube 10') mentioned above, and the Debye rings C and C', which can be obtained on the sensor 20 due to that. Thus, FIGS. 5A and 5B show a case of irradiating the X-ray and the X'-ray directing upon the sample surface while disposing the pair of X-ray tubes 10 and 10' at the central portions on both sides of the semiconductor X-ray sensor portion 20, and thereby the Debye rings C and C' can be obtained along both upper and low sides of the semiconductor X-ray sensor portion 20, respectively. On the other hand, FIGS. 6A and 6B show a case of disposing the pair of X-ray tubes 10 and 10' along a diagonal line of the semiconductor X-ray sensor portion 20, and in that case, as is shown in FIG. 6A, the Debye rings C and C' can be obtained, respectively, along a diagonal line perpendicular to that mentioned above. Also, as is shown in FIGS. 7A and 7B, it can be seen that the respective Debye rings C and C' can be obtained on the semiconductor X-ray sensor portion 20, in a case of disposing the pair of X-ray tubes 10 and 10' along one (1) side of the semiconductor X-ray sensor portion 20.

Further, as was mentioned above, since a relationship of disposing the semiconductor X-ray sensor portion 20 and the pair of X-ray tubes (e.g., the first X-ray tube 10 and the second X-ray tube 10'), in other words, angles for inclining the semiconductor X-ray sensor portion 20 with respect to the X-ray and the X'-ray and/or distances from each pixel on the surface thereof are determined, in advance, therefore, it is possible to specify or identify the radiuses of the Debye rings C and C', or the angles of the cones (π-2θ, π-2θ'), easily, upon basis of the positions (x,y) of the pixels detecting the diffracted X-ray on the semiconductor X-ray sensor portion 20 mentioned above. For example, while memorizing pixel positions on the sensor surface, corresponding to plural numbers of Debye rings C and C', which are obtained in advance through calculations thereof, into a memory or the like, and by using this, it is possible to obtain the Debye rings C and C', or the angles of the cones (π-2θ, π-2θ'), in a relatively easy manner, from the diffracted X-ray, which is actually detected on the semiconductor X-ray sensor portion 20.

However, when measuring the stress with using the detected signals, each of which can be obtained from each pixel of the semiconductor X-ray sensor portion 20 mentioned above, it is important to specify or identify to which one of the plural numbers of the Debye rings C and C' mentioned above the X-ray beam detected by those pixels belongs. Further, the specification or identification of the Debye rings may be executed by means of such information processing device or portion 25 as was mentioned above, then hereinafter, detailed explanation will be given on a method for identifying the Debye rings C and C', in particular, in case where they intersect with each other.

Figure 8A:
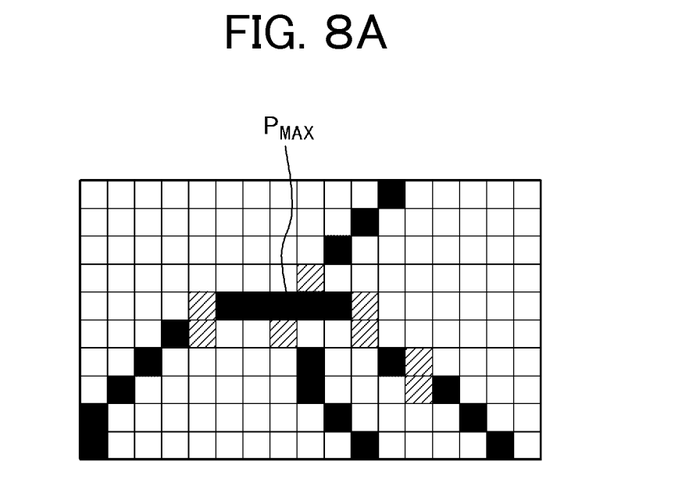
FIGS. 8A and 8B are views for showing a method for identifying to which one of the pair of X-ray tubes the Debye ring belongs, from signals detected by pixels of the sensor portion mentioned above.
Figure 8B:
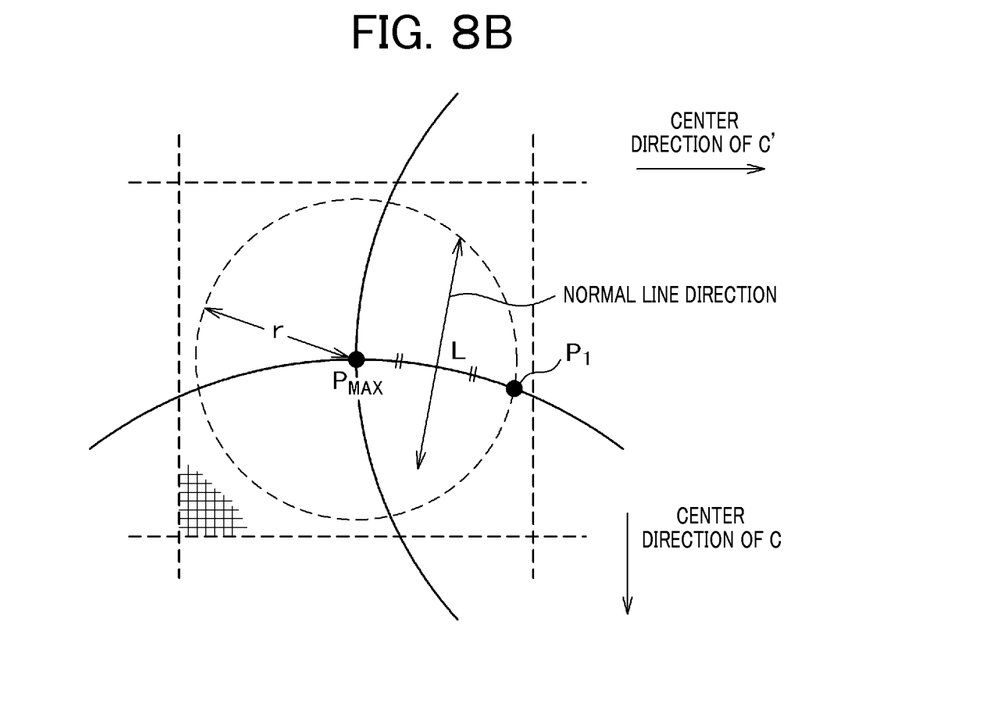

FIG. 8A shows an enlarged part of the large number of pixels, being formed on the surface of the semiconductor X-ray sensor portion 20 mentioned above. Firstly, an entire of the sensor surface is divided into plural numbers of areas or regions, and wherein a seek out is made on a pixel (s) showing the strongest intensity of X-ray among the pixels within a respective region (for example, a pixel, at which two (2) Debye rings C and C' overlap each other, etc.: $P_{MAX}$ in the example shown in the figure). Thereafter, as is shown in FIG. 8B, centering around this point as a center, a seek out is also made on a pixel (s) (e.g., $P_1$) showing the next coming intensity of X-ray, for example, about a half of the maximum intensity of X-ray mentioned above, within peripheral portions separating from that center by a predetermined distance=r (or example, 20 pixels, approximately), and a line is drawn at a middle point between those two (2) points; thereby obtaining a direction of a normal line. As a result, it is determined if the center of the Debye ring, which is calculated in advance, is located or not, in the direction of the normal line (with a tolerance limit of about 10%, for example), and thereby determining to which one of the two (2) Debye rings C and C' the X-ray beam detected by the pixels belongs. However, in this example is shown the case where the Debye ring C' is detected by means of the pixels. Further, such processing as was mentioned above is executed on the areas or regions divided, and thereby making the determination on all of the Debye rings, which are formed on the surface of the semiconductor X-ray sensor portion 20.

Figure 9A:
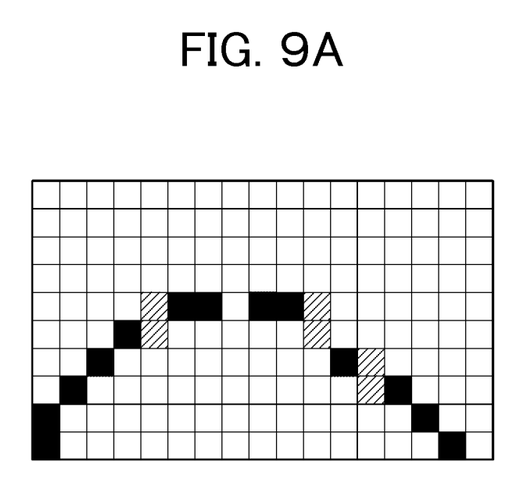
FIGS. 9A and 9B are views for showing the case where the Debye ring belonging to one of the X-ray tubes is removed from a detection signal of each pixel of the sensor portion mentioned above.
Figure 9B:
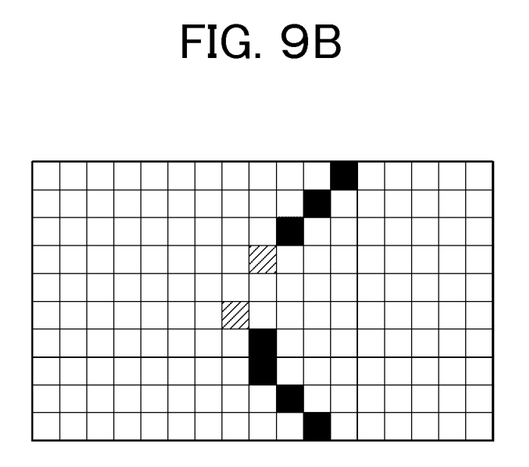

As a result of the mentioned above, the plural numbers of the Debye rings, which are detected on the surface of the semiconductor X-ray sensor portion 20 mentioned above, are classified into (1) the Debye ring C centering around the first X-ray tube 10, (2) the Debye ring C' centering around the second X-ray tube 10', and further (3) a portion caused due to both X-ray tubes 10 and 10', and (4) a portion not relating to any X-ray tube. Then, when analyzing the Debye ring C centering around the first X-ray tube 10, as is shown in FIG. 9A, it is enough to pick up the Debye ring C of the above (1) from the plural numbers of Debye rings, which are detected on the surface of the sensor portion 20, while removing those of the above (2)-(4) therefrom. Also, when analyzing the Debye ring C' centering around the second X-ray tube 10', as is shown in FIG. 9B, it is enough to pick up the Debye ring C' of the above (2) from the plural numbers of Debye rings, which are detected on the surface of the sensor portion 20, while removing those of the above (1) and (3)-(4) therefrom. With doing this, it is also possible to apply general software for use of stress analysis of diffraction of X-ray, thereafter.

Further, hereinafter, explanation will be given on a variation of the hand-held type X-ray stress measuring apparatus according to the one embodiment of the present invention, which was mentioned in the details thereof in the above.

Figure 10:
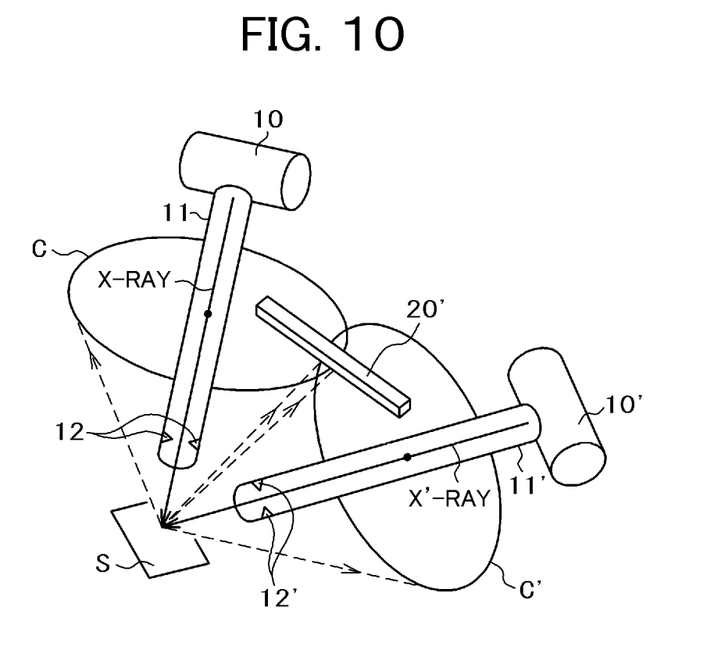
FIG. 10 is a perspective view for showing an arrangement of the semiconductor X-ray sensor portion and the pair of the X-ray tubes, within the X-ray stress measuring apparatus according to other embodiment of the present invention.

First of all, FIG. 10 shows a part of the structures of applying a 1-dimensional (i.e., a line) X-ray sensor 20', in the place of the 2-dimensional (i.e., the area) X-ray sensor 20 mentioned above, as the semiconductor X-ray sensor portion thereof, in particular, in the embodiment shown in FIG. 1 mentioned above. However, other portions of the structures in the figure are almost similar to those mentioned above, and therefore the detailed explanations thereof will be omitted herein. But, also within this variation, it is possible to detect the Debye rings C and C' (i.e., the diffraction cones), being formed at the position where they are adjacent to each other or they intersect with each other, on the semiconductor X-ray sensor portion 20' mentioned above, by driving the pair of X-ray tubes (e.g., the first X-ray tube 10 and the second X-ray tube 10') (i.e., entering or irradiating the X-ray and the X'-ray), and it is also possible to measure the stress, by measuring the radiuses of those Debye rings C and C'.

Further, if adopting such structures as was mentioned above, in other words, applying the 1-dimensional (i.e., the line) X-ray sensor 20' in the place of the 2-dimensional (i.e., the area) X-ray sensor 20, in the semiconductor X-ray sensor portion, it is possible to achieve further small-sizing and weight-reducing of the apparatus. However, as was mentioned above, in particular, when measuring the stress with using the detected signals, each of which can be obtained from each pixel of the semiconductor X-ray sensor portion 20', it is important to specify or identify to which one of the plural numbers of Debye rings C and C' mentioned above the X-ray beams detected by those pixels belongs.

Figure 11:
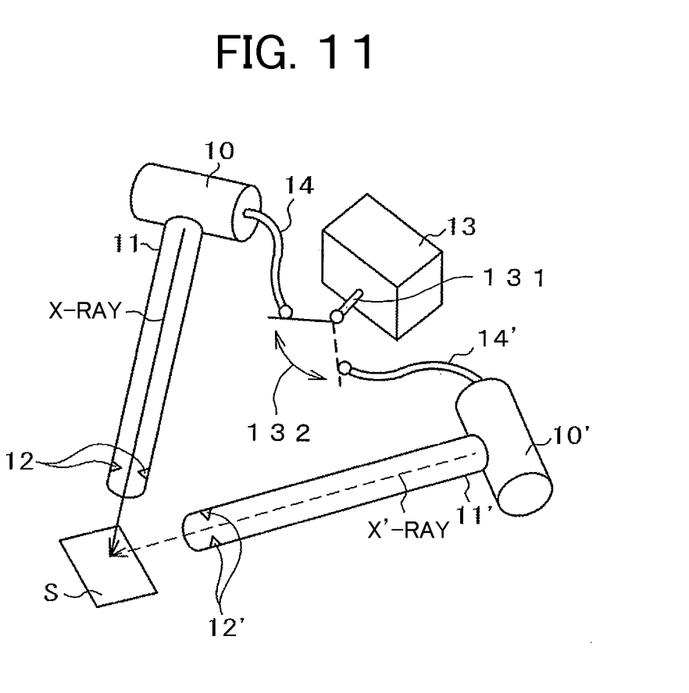
FIG. 11 is a perspective view for explaining the outputting structure of one (1) piece of a high-voltage generating portion, within the X-ray stress measuring apparatus according to the embodiment mentioned above.

Then, according to this variation, as is shown in FIG. 11 attached herewith, a switch 132 is attached onto an output terminal 131 of one (1) piece of the high-voltage generating portion 13. And, the high-voltage from the one (1) piece of the high-voltage generating portion 13 is supplied to the first X-ray tube 10 or the second X-ray tube 10', sequentially, being exchanged by the switch 132 attached to that output terminal, through high-voltage cables 14 and 14'. However, exchanging of this switch 132 is controlled by, such as, a controller portion 320, with using a clock signal therein, for example, responding to push-down of the trigger (switch) 450 mentioned above. With this, since the first X-ray tube 10 and the second X-ray tube 10' generate the X-ray beams, but in time zones different from each other, respectively, it is possible for the 1-dimensional (i.e., the line) X-ray sensor 20' to measure the plural numbers of Debye rings C and C', selectively, in the time zones different from each other. Thus, even if applying the 1-dimensional (i.e., the line) X-ray sensor 20' as the semiconductor X-ray sensor portion, it is possible to measure the X-ray beam, with specifying or identifying to which one of the plural numbers of Debye rings C and C' it belongs (i.e., to the X-ray from the first X-ray tube 10, or to the X-ray from the second X-ray tube 10'), with certainty.

As was fully mentioned in the details thereof in the above, according to the present invention, it is possible to achieve small-sizing and/or weight-reducing of the apparatus, with applying the 2-dimensional (i.e., the area) X-ray detector, which becomes relatively large in the sizes thereof, including the relating parts thereof, or the 1-dimentional (i.e., the line) X-ray detector, appropriately, and there by brings about a superior effect of providing the hand-held type X-ray stress measuring apparatus of being actually portable.

Also, with the embodiments mentioned in the above, the explanation was given that the signal processing portion 25, inputting parts of the Debye rings C and C' therein, as the electric signals, for treating the predetermined processing thereon to be outputted, is attached within an inside of the radiation shield 100 mentioned above; however, the present invention should not be restricted only to this, this may be disposed in an outside thereof. Or, at the tip portion thereof, at which the radiation shield 100 comes in contact on the surface of the sample S, it is also possible to attach an opening portion made of an elastic material, such as, a rubber, etc., for example, for maintaining air tightness within the shied. In addition thereto, not shown in the figure, if attaching an image pickup means (for example, a CCD camera) for photographing the surface of the sample, in an inside of the radiation shield 100 mentioned above, together with a light source for illumination thereof, it is also possible to show an image of the sample surface, which is taken in by that image pickup means on the display portion (for example, the liquid crystal display device) 310 mentioned above. Furthermore, it is also possible to alter constituent part(s), other than that mentioned above, appropriately, in the similar manner, as far as it/they can achieve the inherent function(s) thereof.

EXPLANATION OF MARKS

10, 10' . . . X-ray tube, 11, 11' . . . collimator, 12, 20 . . . semiconductor sensor portion (2-dimensional (area) X-ray sensor), 20' . . . 1-dimensional (line) X-ray sensor, 13, 13' . . . high-voltage generating portion, 25 . . . signal processing portion, 310 . . . display portion, 400 . . . power source portion, 410 . . . battery (rechargeable battery), 450 . . . trigger (switch), 460 . . . grip portion, C, C' . . . Debye ring, S . . . sample.

What is claimed is:

1. An X-ray stress measuring apparatus, for measuring stress on a sample, comprising:
   a pair of X-ray generating means for irradiating X-ray beams, which are disposed with a first predetermined angle defined between the X-ray beams, on a plane inclined by a second predetermined angle with respect to a surface of the sample to be measured;
   an X-ray sensor portion for detecting plural numbers of Debye rings, generated upon irradiation of X ray beams from said pair of X-ray generating means; and
   a battery means for supplying electricity to said pair of X-ray generating means and said X-ray sensor portion, wherein said X-ray sensor portion is comprised of a 2 dimensional X-ray detector or a 1-dimensional X-ray detector, and is disposed in a position where the plural numbers of Debye rings, generated by the interaction of the incident X-ray beams from said at least one pair of X-ray generating means and the sample, are adjacent to each other, or intersect with each other.

2. The X-ray stress measuring apparatus, as described in claim 1, wherein the first predetermined angle between the X-ray beams of said pair of X-ray generating means is within a range from 20 degrees to 170 degrees.

3. The X-ray stress measuring apparatus, as described in claim 2, wherein the first predetermined angle between the X-ray beams of said pair of X-ray generating means is 90 degrees.

4. The X-ray stress measuring apparatus, as described in claim 1, wherein said X-ray sensor portion comprised of the 2-dimensional X-ray detector, further comprises means for determining which of the X-ray beams is incident upon the sample from said pair of X-ray generating means based on the Debye rings detected by said 2-dimensional X-ray detector.

5. The X-ray stress measuring apparatus, as described in claim 4, wherein said 2-dimensional X-ray detector is fixed at a position and an angle, which are predetermined with respect to said pair of X-ray generating means, within a space defined between said pair of X-ray generating means.

6. The X-ray stress measuring apparatus, as described in claim 1, wherein said X-ray sensor portion comprising the 1-dimensional X-ray detector, further comprises means for driving said pair of X-ray generating means, selectively, in sequence.

7. The X-ray stress measuring apparatus, as described in claim 6, wherein said 1-dimensional X-ray detector is fixed at a position and an angle, which are predetermined with respect to said pair of X-ray generating means, within a space defined between said pair of X-ray generating means.

8. The X-ray stress measuring apparatus, as described in claim 1, further comprising a radiation shielding member for storing said X-ray sensor portion together with said pair of X-ray generating means therein.

9. The X-ray stress measuring apparatus, as described in claim 8, further comprising a grip portion attached on said radiation shielding member combined in one body.

10. The X-ray stress measuring apparatus, as described in claim 9, further comprising a trigger disposed in a position adjacent to said grip portion, for instructing an X-ray stress measuring operation of said X-ray stress measuring apparatus.

11. The X-ray stress measuring apparatus, as described in claim 9, wherein said battery means is stored within said grip portion, and further, said battery means is a rechargeable battery.

12. The X-ray stress measuring apparatus, as described in claim 8, further comprising a display portion for displaying a result of an X-ray stress measurement by said X-ray stress measuring apparatus, outside of said radiation shielding member.

* * * * *